US012599559B2

(12) United States Patent
Ishii et al.

(10) Patent No.: US 12,599,559 B2
(45) Date of Patent: Apr. 14, 2026

(54) CD1d-LIGAND-COMPOUND-CONTAINING LIPOSOME PREPARATION HAVING IMPROVED PHARMACOKINETICS

(71) Applicants: REGiMMUNE Corporation, Tokyo (JP); Osaka University, Suita (JP)

(72) Inventors: Yasuyuki Ishii, Tokyo (JP); Takashi Matsuzaki, Suita (JP)

(73) Assignees: REGiMMUNE Corporation, Tokyo (JP); Osaka University, Suita (JP)

( * ) Notice: Subject to any disclaimer, the term of this patent is extended or adjusted under 35 U.S.C. 154(b) by 334 days.

(21) Appl. No.: 18/255,158

(22) PCT Filed: Dec. 2, 2021

(86) PCT No.: PCT/JP2021/044231

§ 371 (c)(1),
(2) Date: May 31, 2023

(87) PCT Pub. No.: WO2022/118913

PCT Pub. Date: Jun. 9, 2022

(65) Prior Publication Data

US 2023/0414507 A1 Dec. 28, 2023

(30) Foreign Application Priority Data

Dec. 4, 2020 (JP) ................................ 2020-201802

(51) Int. Cl.
*A61K 9/127* (2025.01)
*A61K 31/7032* (2006.01)

(52) U.S. Cl.
CPC .......... *A61K 9/127* (2013.01); *A61K 31/7032* (2013.01)

(58) Field of Classification Search
None
See application file for complete search history.

(56) References Cited

U.S. PATENT DOCUMENTS

2004/0009216 A1 1/2004 Rodrigueza et al.
2007/0104776 A1 5/2007 Ishii et al.
2015/0283235 A1 10/2015 Hirai et al.
2017/0232390 A1 8/2017 Matsuzaki et al.
2019/0231822 A1* 8/2019 Blazar .................. A61K 9/0019
2021/0259971 A1* 8/2021 Matsuzaki ............. A61K 45/06

FOREIGN PATENT DOCUMENTS

JP 2005-527582 A 9/2005
JP 2025-527582 A 9/2005
WO 2003/086351 A1 10/2003
WO WO 2005/120574 A1 12/2005
WO WO 2014/069655 A1 5/2014
WO WO 2016/024510 A1 2/2016
WO WO 2018/013971 A1 1/2018
WO WO 2019/088193 A1 5/2019
WO WO 2019/107431 A1 6/2019

OTHER PUBLICATIONS

Chen et al., "Increased Foxp3$^+$Helios$^+$ Regulatory T Cells and Decreased Acute Graft-versus-Host Disease after Allogeneic Bone Marrow Transplantation in Patients Receiving Sirolimus and RGI-2001, an Activator of Invariant Natural Killer T Cells," *Biol. Blood Marrow Transplant*, 23(4): 625-634 (2017).
De Serrano et al., "Liposomal Vaccine Formulations as Prophylactic Agents: Design Considerations for Modern Vaccines," *J. Nanobiotechnology*, 15(1): 83 (2017).
Du et al., "Invariant natural killer T cells ameliorate murine chronic GVHD by expanding donor regulatory T cells," *Blood*, 129(23): 3121-3125 (2017).
Duramad et al., "Pharmacologic Expansion of Donor-Derived, Naturally Occurring CD4$^+$Foxp3$^+$ Regulatory T Cells Reduces Acute Graft-versus-Host Disease Lethality Without Abrogating the Graft-versus-Leukemia Effect in Murine Models," *Biol. Blood Marrow Transplant*, 17(8): 1154-1168 (2011).
Ishii et al., "Alpha-galactosylceramide-driven immunotherapy for allergy," *Front. Biosci.*, 13(16): 6214-6228 (2008).
Hirai et al., "A Novel Approach Inducing Transplant Tolerance by Activated Invariant Natural Killer T Cells With Costimulatory Blockade," *Am. J. Transplant.*, 14(3): 554-567 (2014).
Hirai et al., "Clonal Deletion Established via Invariant NKT Cell Activation and Costimulatory Blockade Requires In Vivo Expansion of Regulatory T Cells," *Am. J. Transplant.*, 16(2): 426-439 (2016).
Oku et al., "Real-time analysis of liposomal trafficking in tumor-bearing mice by use of positron emission tomography," *Biochim. Biophys. Acta.*, 1238(1): 86-90 (1995).
Tamura et al., "Characterization of the immature dendritic cells and cytotoxic cells both expanded after activation of invariant NKT cells with α-galactosylceramide in vivo," *Biochem. Biophys. Res. Commun.*, 369(2): 485-492 (2008).
Japan Patent Office, International Search Report in International Patent Application No. PCT/JP2021/044231 (Feb. 15, 2022).
European Patent Office, Extended European Search Report in European Patent Application No. 21900664.0 (Oct. 9, 2024).
De Serrano et al., "Liposomal Vaccine Formulations as Prophylactic Agents: Design Considerations for Modern Vaccines," Nanobiotechnology, 15: 83 (2017).
Regimmune, "REGiMMUNE Initiates Phase I/II Clinical Trial for GvHD," Marketwire Press Release, FirstWord Pharma (Feb. 1, 2012).

* cited by examiner

*Primary Examiner* — Celeste A Roney
(74) *Attorney, Agent, or Firm* — Leydig, Voit & Mayer, Ltd.

(57) ABSTRACT

The present invention provides a liposome preparation containing a population of liposomes containing a CD1d ligand compound, wherein the average particle size of the population of liposomes is 90 to 110 nm and the polydispersity index of particle size distribution is 0.2 or less. and the polydispersity index of the particle size distribution is 0.2 or less. The present invention also provides the use of the liposome preparation in the prevention or treatment of graft-versus-host disease and organ transplant rejection.

20 Claims, 3 Drawing Sheets

CD1d-LIGAND-COMPOUND-CONTAINING LIPOSOME PREPARATION HAVING IMPROVED PHARMACOKINETICS

TECHNICAL FIELD

The present invention relates to a liposome preparation containing a CD1d ligand compound with improved pharmacokinetics. More particularly, the invention relates to a liposome preparation containing a CD1d ligand compound having pharmacokinetics improved by adjusting the particle size to be uniform.

BACKGROUND ART

Graft-versus-host disease (GVHD) is a complication of allogeneic hematopoietic stem cell transplantation in which donor-derived lymphocytes attack recipient organs as if they were foreign substances. GVHD is a disease in which the blood donor's immune system attacks and destroys the blood recipient's systemic tissues and there are two types including acute GVHD in the early stage of transplantation and chronic GVHD in the late stage of transplantation. GVHD is also known to be caused by blood transfusion.

$CD4^+CD25^+Foxp3^+$ regulatory T cell (Treg) is thought to be a key player in maintaining central and peripheral immune tolerance. Animal experimental studies have shown that this cell prevents or ameliorates T cell-mediated diseases such as autoimmune diseases and graft rejection by restoring immune tolerance to alloantigens as well as self-antigens. Studies in both humans and mice have demonstrated a pivotal role of Tregs in the regulation of GVHD. However, the development of therapeutic modalities based on Tregs has been hindered due to the small size of this cell population. The discovery of molecules that efficiently increase functional Tregs in vivo may contribute to the development of novel therapeutics to treat GVHD as well as other immune diseases. A variety of strategies to activate and increase Tregs in situ are emerging.

α-galactosylceramide (α-GalCer) functions as a ligand for the CD1d molecule expressed on antigen-presenting cells. The CD1d molecule is an invariant tumor histocompatibility complex (MHC) class I like antigen presenting molecule with an antigen-binding groove adopted for the presentation of lipid antigens. When α-GalCer is presented on CD1d molecules expressed on various cell types such as dendritic cells (DCs), macrophages, and B cells, it is recognized by the invariant T cell (TCR) expressed on invariant NKT (iNKT) cells and activates iNKT cells in a CD1d-restricted manner. The CD1d-restricted activation of iNKT cells results in rapid and massive release of both Th1 and Th2 cytokines, and this is a unique feature that distinguishes iNKT cells from conventional T cells and suggests an important immunoregulatory function in both innate and acquired immunity. KRN7000 ((2S,3S,4R)-1-o-(α-D-galactopyranosyl)-2-(N-hexacosanoylamino)-1,3,4-octadecanetriol) is a synthetic derivative of α-GalCer originally discovered in marine sponges.

Although KRN7000 has been shown to act as an immunostimulant in its aqueous form, a liposome preparation of KRN7000 was found to induce antigen-specific immunosuppression or tolerance (Patent Document 1, Non-Patent Documents 1 and 2). Previous studies suggested that targeting a different cell with the liposomal KRN7000 resulted in a different immunomodulatory response. That is, aqueous KRN7000 was presented mainly on DCs and consequently stimulated iNKT cells in the presence of IL-12 secreted from DCs. In contrast, liposomal KRN7000 was presented mainly on B cells and its interaction with iNKT cells induced IL-10 production by both iNKT and B cells, leading to proliferation of immune tolerogenic DCs (Non-Patent Document 1). Subsequently, induction of antigen-specific $CD4^+CD25^+$ $Foxp3^+$ cell production was observed in the presence of a model antigen, ovalbumin (Non-Patent Documents 1 and 2). The lipid composition of the liposome was thought to enhance the uptake of liposomal KRN7000 by B cells, which may have distorted the immune response in the direction of tolerance.

The present inventors have shown that liposomal KRN7000 (RGI-2001) can induce alloantigen-specific tolerance through Treg induction (Non-Patent Document 3). In a mouse acute GVHD model, a single dose of RGI-2001 markedly prolonged mouse survival. Enhanced proliferation of donor-derived CD4+Foxp3+ Tregs was found to be a key mechanism. Host alloantigen-specific immunosuppression was induced early after bone marrow transplantation (BMT), but responses to third-party alloantigens and leukocytes were not suppressed. Furthermore, RGI-2001 was also found to reduce symptoms in a mouse chronic GVHD model. These results indicated that RGI-2001 may be a new therapeutic option to prevent both acute and chronic GVHD (Non-Patent Document 4).

The applicability of RGI-2001 to GVHD has also been confirmed in a human clinical trial (Non-Patent Document 5). A phase 1/2a clinical trial was conducted in which 29 patients who had received allogeneic hematopoietic stem cell transplantation were treated with a single intravenous dose of RGI-2001 on day 0. In some patients treated with RGI-2001, the number of Tregs (CD4+CD25+ CD127loFoxp3+) was markedly elevated within 1 to 3 weeks after transplantation. GVHD was more strongly reduced in responders with increased Tregs counts compared to non-responders.

The applicability of RGI-2001 to organ transplantation has been confirmed in a mouse heart transplantation model (Non-Patent Documents 6 and 7). By administering RGI-2001 and CD40-CD40L blocking antibodies simultaneously to recipient mice when the recipient mice were irradiated with sublethal dose of radiation and engrafted with spleen and bone marrow cells from donor mice, bone marrow chimeras were established in recipient mice and suppression on rejection of donor-derived heart and skin was maintained for a long time.

Patent document 2 discloses a liposome production technology that can easily control the concentration of a dialyzed solution (e.g., liposome solution) after dialysis in the dialysis process using a hollow fiber dialysis column to obtain a dialyzed solution (e.g., liposome solution) with a desired concentration.

Patent Document 3 discloses a technique for producing lipid particles which comprises performing a primary dilution of an alcohol-containing solution in which the lipid is dissolved at an alcohol concentration at which the lipid particles are destabilized, and performing a secondary dilution to obtain stabilized lipid particles in which the particle size of the lipid particles can be controlled while maintaining a uniform particle size distribution by adjusting the retention time from the primary dilution to the secondary dilution.

Non-Patent Document 8 discloses results of analyzing the pharmacokinetics of liposomes with various particle sizes using PET technology.

CITATION LIST

Patent Documents

Patent document 1: WO2005/120574 A1
Patent document 2: WO2016/024510 A1
Patent document 3: WO2019/088193 A1

Non-Patent Documents

Non-Patent Document 1: Tamura Y et al., Biochem Biophys Res Commun 369: 485-492, 2008
Non-Patent Document 2: Ishii Y et al, Front Biosci 13: 6214-6228, 2008
Non-Patent Document 3: Duramad O et al., Biol Blood Marrow Transplant 17: 1154-1168, 2011
Non-Patent Document 4: Du Jing et al., Blood 129: 3121-3125, 2017
Non-Patent Document 5: Chen Y B et al., Biol Blood Marrow Transplant 23: 625-634, 2017
Non-Patent Document 6: Hirai et al., Am J Transplant 14: 1154-1168, 2014
Non-Patent Document 7: Hirai et al., Am J Transplant 16: 426-439, 2016
Non-Patent Document 8: Oku, N et al., Biochim. Biophys. Acta, 1238: 86-90, 1995

SUMMARY OF THE INVENTION

Problems to be Solved by the Invention

As mentioned above, in the Phase 1/2a clinical trial of liposomal KRN7000 for the prevention of GVHD, some patients showed a remarkable therapeutic response, while others did not show a satisfactory response. Investigations into the cause of this have been conducted and it has revealed that pharmacokinetics were unstable and plasma KRN7000 concentration was low from immediately after administration, and it then rose once but fell again. These results suggest that prolonged blood retention from immediately after administration is important for liposomal KRN7000 to fully exert its efficacy, and that the formulation used in the Phase 1/2a clinical trial (RGI-2001-001) may not meet these conditions.

The present invention aims to provide a liposome preparation containing a CD1d ligand that can be retained in the blood for a long period and maintain a high blood CD1d ligand concentration for a long period.

Means to Solve the Problems

The present inventors have diligently studied to solve the above problem and found that the instability in hemodynamics was caused by the particle size of the liposomes used in the Phase 1/2a clinical trial. The average particle size of the liposomes in the liposomal KRN7000 preparation (RGI-2001-001) used in the Phase 1/2a clinical trial was about 120 nm. A liposome preparation (RGI-2001-003) with average particle size converged to around 100 nm was newly prepared without changing KRN7000 content and lipid composition from RGI-2001-001 and administered intravenously to patients after hematopoietic stem cell transplantation. Surprisingly, the pharmacokinetics was improved, the maximum blood concentration of KRN7000 was increased, and the blood half-life was successfully extended. These preparations were administered intravenously to mice, and plasma IFN-γ and IL-4 concentrations were measured. Though IL-4 was higher in the RGI-2001-003 administration group than in the RGI-2001-001 administration group, IFN-γ was lower in the RGI-2001-003 administration group rather than in the RGI-2001-001 administration group, indicating that RGI-2001-003 may have a property of inducing Tregs more effectively. Based on these findings, the present inventors further investigated and completed the present invention.

That is, the present invention relates to the followings:

[1] A liposome preparation containing a population of liposomes containing a CD1d ligand compound, wherein the average particle size of the population of liposomes is 90 to 110 nm, and the polydispersity index of the particle size distribution is 0.2 or less.

[2] The liposome preparation of [1], wherein the average particle size is 92.9 to 101.0 nm.

[3] The liposome preparation of [1] or [2], wherein the polydispersity index of the particle size distribution is 0.133 or less.

[4] The liposome preparation of any of [1] to [3], wherein the number of liposomes having a particle size of less than 50 nm is 10% or less of the total population of liposomes.

[5] The liposome preparation of any of [1] to [4], wherein the number of liposomes having a particle size of more than 450 nm is 10% or less of the total population of liposomes.

[6] The liposome preparation of any of [1] to [5], wherein the average particle size is maintained at 90 to 110 nm for at least 1 month under the conditions of a temperature of 25° C. and a relative humidity of 60% RH.

[7] The liposome preparation of any of [1] to [6], wherein the CD1d ligand compound is α-galactosylceramide.

[8] The liposome preparation of [7], wherein the α-galactosylceramide is (2S,3S,4R)-1-o-(α-D-galactopyranosyl)-2-(N-hexacosanoylamino)-1,3,4-octadecanetriol.

[9] The liposome preparation of any of [1] to [8], wherein the population of liposomes is contained as a liposome suspension.

[10] The liposome preparation of [9], wherein the pH of the liposome suspension is 5.8 to 6.8.

[11] The liposome preparation of any of [1] to [8], wherein the population of liposomes is contained as a lyophilized product.

[12] The liposome preparation of any of [1] to [11], which is for injection administration.

[13] The liposome preparation of any of [1] to [12], which is for prevention or treatment of graft-versus-host disease.

[14] The liposome preparation of [13], wherein the graft-versus-host disease is caused by allogeneic hematopoietic stem cell transplantation.

[15] The liposome preparation of any of [1] to [12], which is for prevention or treatment of organ transplant rejection.

[16] The liposome preparation of [15], wherein the organ transplant is a transplant of an allogeneic organ or cell.

[17] The liposome preparation of [15], wherein the organ transplant is a transplant of a xenogeneic organ or cell.

[18] A method for reducing the risk of developing graft-versus-host disease in a subject having a risk of developing graft-versus-host disease, comprising administering an effective amount of the liposome preparation of any of [1] to [12] to the subject.

[19] The method of [18], wherein the subject having a risk of developing graft-versus-host disease is a subject who has received an allogeneic tissue or cell transplant or is scheduled to receive an allogeneic tissue or cell transplant.

[20] A method for treating graft-versus-host disease in a subject who has developed graft-versus-host disease, comprising administering an effective amount of the liposome preparation of any of [1] to [12] to the subject.

[21] The method of any of [18] to [20], wherein the graft-versus-host disease is caused by allogeneic hematopoietic stem cell transplantation.

[22] A method for reducing the risk of developing organ transplant rejection in a subject having a risk of developing organ transplant rejection, comprising administering an effective amount of the liposome preparation of any of [1] to [12] to the subject.

[23] The method of [22], wherein the subject having a risk of developing organ transplant rejection is a subject who has received a transplant of an allogeneic or xenogeneic organ or cell or is scheduled to receive a transplant of an allogeneic or xenogeneic organ or cell.

[24] A method of treating an organ transplant rejection in a subject who has developed an organ transplant rejection, comprising administering an effective amount of the liposome preparation of any of [1] to [12] to the subject.

[25] The method of any of [22] to [24], wherein the organ transplant is a transplant of an allogeneic organ or cell.

[26] The method of any of [22] to [24], wherein the organ transplant is a transplant of a xenogeneic organ or cell.

[27] The liposome preparation of any of [1] to [12] for use in the prevention or treatment of graft-versus-host disease.

[28] The liposome preparation of [27], where the graft-versus-host disease is caused by allogeneic hematopoietic stem cell transplantation.

[29] The liposome preparation of any of [1] to [12] for use in the prevention or treatment of organ transplant rejection.

[30] The liposome preparation of [29], wherein the organ transplant is a transplant of an allogeneic organ or cell.

[31] The liposome preparation of [29], wherein the organ transplant is a transplant of a xenogeneic organ or cell.

[32] Use of the liposome preparation of any of [1] to [12] in the manufacture of a medicament for the prevention or treatment of graft-versus-host disease.

[33] The use of [32], wherein the graft-versus-host disease is caused by allogeneic hematopoietic stem cell transplantation.

[34] Use of the liposome preparation of any of [1] to [12] in the manufacture of a medicament for the prevention or treatment of organ transplant rejection.

[35] The use of [34], wherein the organ transplant is a transplant of an allogeneic organ or cell.

[36] The use of [34], wherein the organ transplant is a transplant of a xenogeneic organ or cell.

Effect of the Invention

The present invention provides a liposome preparation containing a CD1d ligand that can be retained in blood for a long period and maintain a high concentration of a CD1d ligand in the blood for a long period. Since the liposome preparation of the present invention may effectively induce Tregs, excellent preventive or therapeutic effects against GVHD, organ transplant rejection, autoimmune disease or the like can be expected.

DESCRIPTION OF EMBODIMENTS

Figure 1:
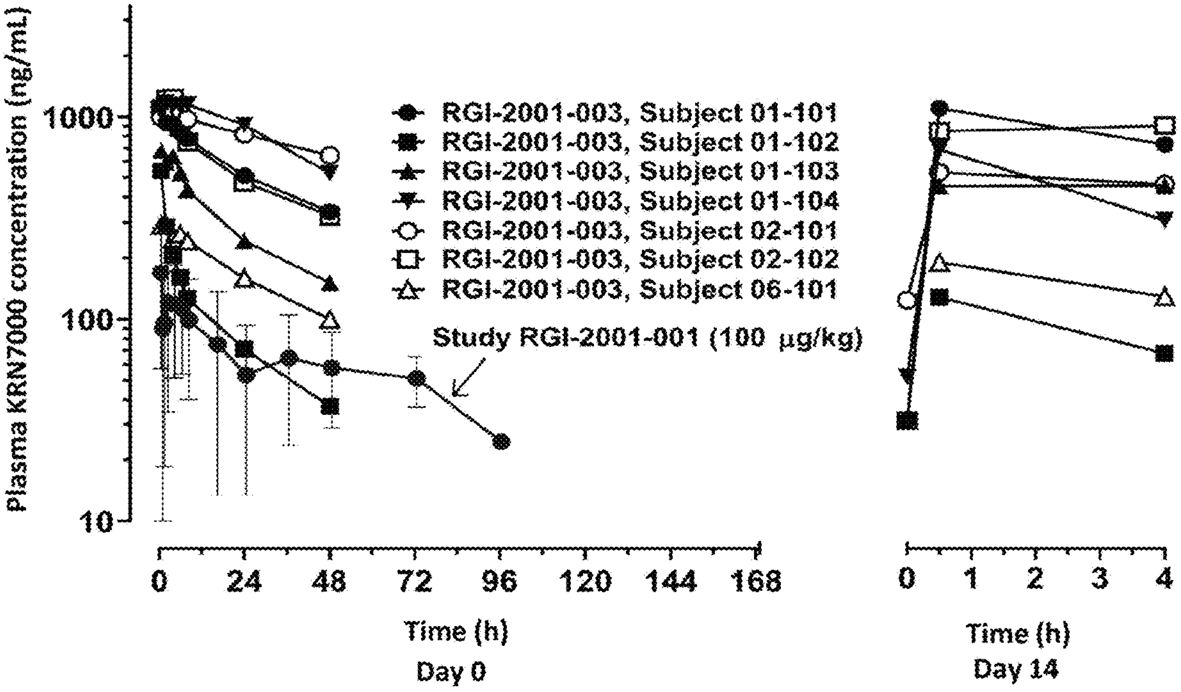
FIG. 1 shows changes in blood KRN7000 concentration in patients administered with RGI-2001 after hematopoietic stem cell transplantation.

The present invention provides a liposome preparation comprising a population of liposomes containing a CD1d ligand compound.

The term "liposome preparation" means a pharmaceutical composition containing an active ingredient encapsulated in a liposome.

The term "population of liposomes" refers to a set of multiple liposomes. The number of liposomes constituting the population of liposomes of the present invention is usually $10^3$ or more (e.g., $10^4$ or more, $10^5$ or more, $10^6$ or more, $10^7$ or more, $10^8$ or more, $10^9$ or more, $10^{10}$ or more, $10^{11}$ or more, or $10^{12}$ or more). The upper limit of the number of liposomes constituting the population of liposomes is not particularly limited, but may be, for example, $10^{21}$ or less, $10^{20}$ or less, $10^{19}$ or less, $10^{18}$ or less, $10^{17}$ or less, or $10^{16}$ or less.

"CD1d ligand compound" means a compound that is recognized by the invariant T cell receptor (NKT cell receptor) on invariant NKT (iNKT) cells and activates the iNKT cells in a CD1d-restricted manner, when presented on a CD1d molecule expressed on antigen-presenting cells (such as dendritic cells (DCs), macrophages, and B cells). Examples of the CD1d ligand compound that can be used in the present invention include α-glycosylceramide, isoglobotrihexosylceramide (Science, 306, p. 1786-1789, 2004), OCH (Nature 413: 531, 2001) or the like, but are not limited to these. α-glycosylceramide is a glycosphingolipid in which a saccharide such as galactose or glucose is bonded to ceramide in the α-configuration. The α-glucosylceramide in which the sugar moiety is galactose is called α-galactosylceramide. Examples of the α-glycosylceramide include those disclosed in WO93/05055, WO94/02168, WO94/09020, WO94/24142, WO98/44928, Science, 278, p. 1626-1629, 1997 or the like, but are not limited thereto.

Examples of the α-glycosylceramide include the compound of the following formula (1), a salt thereof, or a solvate thereof.

(I)

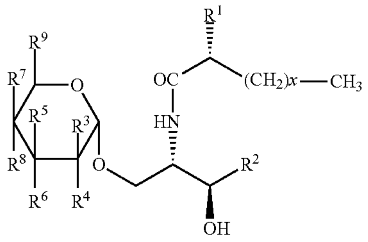

(In the above formula, $R^1$ is H or OH,

X is an integer of 7 to 27, $R^2$ is a substituent selected from the group consisting of (a) to (e) below (wherein Y is an integer of 5 to 17), (a) $—CH_2(CH_2)_YCH_3$, (b) $—CH(OH)(CH_2)_YCH_3$, (c) $—CH(OH)(CH_2)_YCH(CH_3)_2$, (d) $—CH{=}CH(CH_2)_YCH_3$, (e) $—CH(OH)(CH_2)_YCH(CH_3)CH_2CH_3$, and $R^3$ to $R^9$ are substituents defined in i) or ii) below:

i) when $R^3$, $R^6$, and $R^8$ are H, $R^4$ is H, OH, $NH_2$, $NHCOCH_3$, or a substituent selected from the group consisting of the groups (A) to (D) below:

(A)

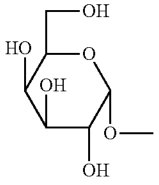

(B)

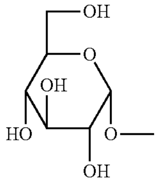

(C)

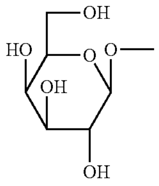

(D)

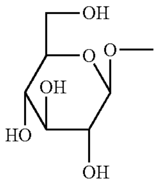

$R^5$ is OH or a substituent selected from the group consisting of the groups (E) and (F) below:

(E)

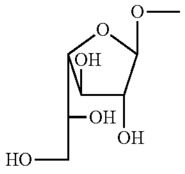

(F)

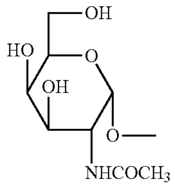

$R^7$ is OH or a substituent selected from the group consisting of the groups (A) to (D) below:

(A)

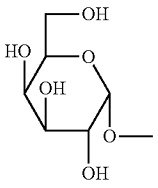

(B)

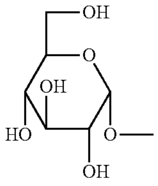

(C)

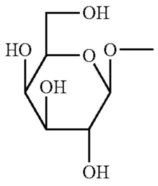

(D)

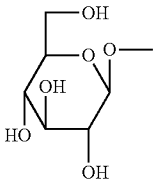

$R^9$ is H, $CH_3$, $CH_2OH$, or a substituent selected from the group consisting of the groups (A') to (D') below:

(A')

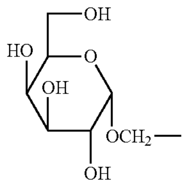

(B')

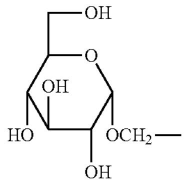

(C')

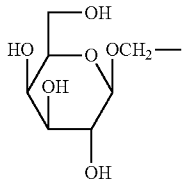

-continued (D')

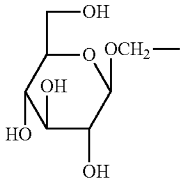

(ii) when $R^3$, $R^6$ and $R^7$ are H, $R^4$ is H, OH, $NH_2$, $NHCOCH_3$ or a substituent selected from the group consisting of the groups (A) to (D) below:

(A)

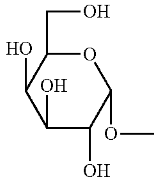

(B)

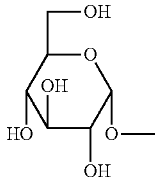

(C)

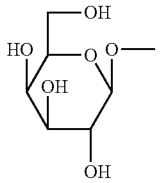

(D)

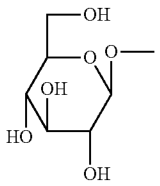

$R^5$ is OH or a substituent selected from the group consisting of the groups (E) and (F) below:

(E)

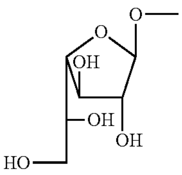

-continued (F)

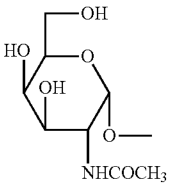

$R^8$ is OH or a substituent selected from the group consisting of the groups (A) to (D) below:

(A)

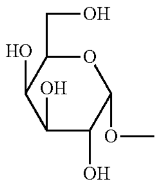

(B)

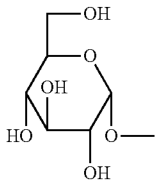

(C)

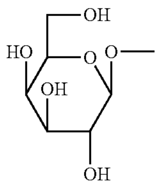

(D)

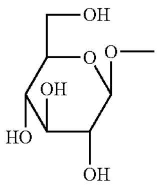

$R^9$ is H, $CH_3$, $CH_2OH$ or a substituent selected from the group consisting, of the groups (A') to (D') below.)

(A')

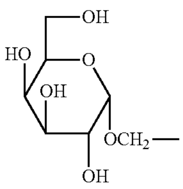

(B')

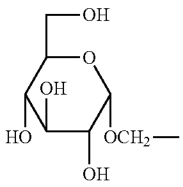

-continued (C')

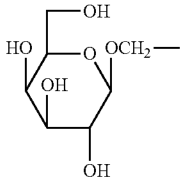

(D')

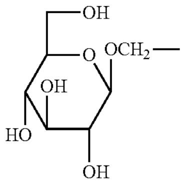

As a α-galactosylceramide, the compound of the above formula (1) wherein $R^3$, $R^6$ and $R^8$ are H, $R^4$, $R^5$ and $R^7$ are OH and $R^9$ is $CH_2OH$, or a salt or solvate thereof can be mentioned.

α-galactosylceramide is preferably (2S,3S,4R)-1-o-(α-D-galactopyranosyl)-2-(N-hexacosanoylamino)-1,3,4-octadecanetriol (also referred to as (2S,3S,4R)-1-O-(α-D-galactosyl)-N-hexacosanoyl-2-amino-1,3,4-octadecanetriol or KRN7000). KRN7000 has the following chemical structure.

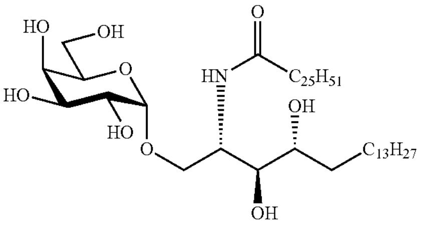

The population of liposomes contained in the liposome preparation of the present invention is characterized in that the average particle size is 90 to 110 nm and the polydispersity index (PdI) of the particle size distribution is 0.2 or less. The present invention is based on the findings that convergence of the particle size of liposomes containing KRN7000 to around 100 nm improves the pharmacokinetics of liposomes administered to patients, increases the maximum blood concentration of KRN7000, and extends its half-life in blood. The average particle size of the population of liposomes of the present invention is 90 nm or more (preferably 91.0 nm or more, 92.0 nm or more, 92.5 nm or more, 92.9 nm or more, 93.0 nm or more, 93.1 nm or more, 93.5 nm or more, 94.0 nm or more, 94.5 nm or more, 94.6 nm or more, 95.0 nm or more, 95.5 nm or more, 95.7 nm or more, 95.8 nm or more, 95.9 nm or more, 96.0 nm or more, or 96.2 nm or more). The average particle size of the population of liposomes of the present invention is 110 nm or less (preferably 109.0 nm or less, 108.5 nm or less, 108.0 nm or less, 107.5 nm or less, 107.0 nm or less, 106.5 nm or less, 106.0 nm or less, 105.5 nm or less, 105.0 nm or less, 104.5 nm or less, 104.0 nm or less, 103.5 nm or less, 103.0 nm or less, 102.5 nm or less, 102.0 nm or less, 101.5 nm or less, or 101.0 nm or less). In one embodiment, the average particle size of the population of liposomes of the present invention is 92.9 to 101.0 nm, 93.1 to 101.0 nm, 93.5 to 101.0 nm, 94.6 to 101.0 nm, 95.7 to 101.0 nm, 95.8 to 101.0 nm, or 95.9 to 101.0 nm.

The population of liposomes contained in the liposome preparation of the present invention is homogeneous with respect to its particle size, and the polydispersity index of the particle size distribution is 0.2 or less (preferably 0.190 or less, 0.180 or less, 0.170 or less, 0.160 or less, 0.150 or less, 0.140 or less, 0.135 or less, 0.133 or less, 0.130 or less, 0.127 or less, 0.125 or less, 0.124 or less, 0.120 or less, 0.116 or less, 0.115 or less, 0.112 or less, 0.110 or less, 0.105 or less, or 0.102 or less).

As used herein, "particle size" is a scale used to represent the size of a particle, and is used as a value corresponding to the diameter if the particle is assumed to be a complete sphere for convenience, as in the meaning that is commonly used in the art. As used herein, "average particle size" may be used to refer to either the number average particle size or the Z-average particle size, but unless otherwise specified, it refers to the Z-average particle size calculated from the measured particle size. As used herein, "particle size distribution" is used in the usual sense used in the art and refers to the spread of particle size. Polydispersity index (PDI) is used as a scale of particle size distribution. The average particle size of the population of liposomes and the polydispersity index of the particle size distribution can be measured by DLS (dynamic light scattering, back-scattering) using Malvern's ZetaSizer Nano ZS (e.g., condition 1 in Experimental Example 5). If necessary, the preparation may be diluted with PBS ($Ca^{2+}$ free).

In a preferred embodiment, in the population of liposomes contained in the liposome preparation of the present invention, the number of liposomes having a particle size of less than 50 nm is 10% or less (e.g., 9% or less, 8% or less, 7% or less, 6% or less, or 5% or less) of the total.

In a preferred embodiment, in the population of liposomes contained in the liposome preparation of the present invention, the number of liposomes having a particle size of more than 450 nm is 10% or less (e.g., 9% or less, 8% or less, 7% or less, 6% or less, 5% or less, 4% or less, 3% or less, 2% or less, 1% or less) of the total.

The liposome constituting the population of liposomes contained in the liposome preparation of the present invention contain a CD1d ligand compound (e.g., KRN7000) as an essential component. The content of a CD1d ligand compound is not particularly limited as long as it is an amount that activates iNKT cells in a subject mammal when the liposome preparation of the present invention is administered to the subject mammal. The content (weight) of a CD1d ligand compound (e.g., KRN7000) in the liposome constituting the population of liposomes of the present invention is for example 1 to 21% (w/w), preferably 5 to 15% (w/w), more preferably 7 to 13% (w/w), further preferably 9 to 11% (w/w) (10±1% (w/w)) of the total weight of components other than the CD1d ligand compound (i.e., lipids) which form the liposomes. In this specification, "components which form liposomes" means, unless otherwise specified, components of the lipid bilayer forming the liposomes and a CD1d ligand compound encapsulated in the liposome, and other components in the inner water phase and outer aqueous phase of liposomes are not included in this term.

The components other than a CD1d ligand compound which form the liposome may be any amphipathic molecules that can form micelles, preferably lipids. Examples of the lipids include, for example, phospholipids including 1,2-dioleoyl-sn-glycero-3-phosphocholine (DOPC), 1,2-dioleoyl-sn-glycero-3-[phospho-rac-(1-glycerol)] sodium salt (DOPG-Na), 1,2-dipalmitoyl-sn-glycero-3-phosphocholine (DPPC), 1,2-dipalmitoyl-sn-glycero-3-[phospho-rac-(1- glycerol)] sodium salt (DPPG-Na) or the like, glycosphingolipids, glyceroglycolipids or the like. These are used alone or in combination of two or more, or in combination with a nonpolar substance such as cholesterol or a lipid derivative in which a water-soluble polymer such as polyethylene glycol is bound to a lipid to prepare the liposomes. In one embodiment, the liposome constituting the population of liposomes of the present invention contains, in addition to a CD1d ligand compound, 1,2-dioleoyl-sn-glycero-3-phosphocholine (DOPC),
1,2-dioleoyl-sn-glycero-3-[phospho-rac-(1-glycerol)] sodium salt (DOPG-Na),
1,2-dipalmitoyl-sn-glycero-3-phosphocholine (DPPC),
1,2-dipalmitoyl-sn-glycero-3-[phospho-rac-(1-glycerol)] sodium salt (DPPG-Na), and cholesterol (Cho).

When the liposome constituting the population of liposomes contained in the liposome preparation of the present invention contain DOPC, DOPG-Na, DPPC, DPPG-Na and Cho, the composition ratio is not particularly limited, but the molar ratio of DOPC:DOPG-Na:DPPC:DPPG-Na:Cho is preferably 15±6:15±6:15±6:15±6:40±16,
more preferably 15±3:15±3:15±3:15±3:40±8, and
further preferably 15±1.5:15±1.5:15±1.5:15±1.5:40±4.

In one embodiment, the liposome constituting the population of liposomes contained in the liposome preparation of the present invention contains a CD1d ligand compound (e.g., KRN7000), DOPC, DOPG-Na, DPPC, DPPG-Na and Cho as lipid bilayer-forming components. In one aspect, the lipid bilayer-forming components of the liposome constituting the population of liposomes of the present invention consist of a CD1d ligand compound (e.g., KRN7000), DOPC, DOPG-Na, DPPC, DPPG-Na, and Cho. In this embodiment, the relative content (weight) of each component is preferably as followings.

KRN7000: 5.0±0.5
DOPC: 9.6±2.4
DOPG-Na: 9.7±2.4
DPPC: 9.0±2.3
DPPG-Na: 9.1±2.3
Cho: 12.6±3.2

The structure of the liposome is not particularly limited as long as it is a vesicle having a lipid bilayer membrane structure, and any liposome, including unilamellar and multilamellar liposomes, may be used.

As a solution to be encapsulated inside the liposome (internal solution), water, a buffer solution, physiological saline, or the like can be used. These solutions can be supplemented with an appropriate amount of water-soluble organic solvents (e.g., glycerin). The internal solution of the liposome may contain an additive such as an osmotic pressure regulator, stabilizer, antioxidant, and pH adjuster.

Examples of the osmotic pressure regulator include, but are not particularly limited to, inorganic salts such as sodium chloride, potassium chloride, sodium hydrogen phosphate, sodium dihydrogen phosphate, and potassium dihydrogen phosphate, polyols such as glycerol, mannitol, and sorbitol, and sorbitol, and saccharides such as glucose, fructose, lactose, and sucrose.

Examples of the stabilizer include, but are not particularly limited to, saccharides such as glycerol, mannitol, sorbitol, lactose, and sucrose, and sterols such as cholesterol.

Examples of the antioxidant include, but are not particularly limited to, ascorbic acid, uric acid, and tocopherol homologs (e.g., vitamin E). While tocopherol has 4 isomers α, β, γ, and δ, any of them can be used in the present invention.

Examples of the pH adjuster include any basic or acidic compound, such as sodium hydroxide, citric acid, acetic acid, triethanolamine, sodium hydrogen phosphate, sodium dihydrogen phosphate, L-histidine and hydrochloride salt thereof.

The internal solution of the liposome is preferably a buffered aqueous solution containing an osmotic pressure regulator and a pH adjuster. The osmotic pressure regulator is preferably sucrose or maltose, and more preferably sucrose. The pH adjuster is preferably L-histidine and hydrochloride salt thereof. The internal solution of the liposome is preferably adjusted to be isotonic or approximately isotonic (e.g., 285±50 mOsm/L) with human body fluid (plasma). When sucrose is used as an osmotic pressure regulator, the sucrose concentration in the internal solution of the liposome is, for example, about 9.0 to 11.0 (10.0±1.0) % (w/v). When maltose is used as an osmotic pressure regulator, the maltose concentration of the internal solution of the liposome is, for example, about 9.0 to 11.0 (10.0±1.0) % (w/v). The pH of the internal solution of the liposome is adjusted to, for example, 5.3 to 7.3 (6.3±1.0), preferably 5.8 to 6.8 (6.3±0.5). In one embodiment, the internal solution of the liposome is a buffered aqueous solution isotonic or approximately isotonic (e.g., 285±50 mOsm/L) to human body fluid (plasma) having a pH of 5.8 to 6.8 (6.3±0.5) containing sucrose, L-histidine and L-histidine hydrochloride, wherein the sucrose concentration is preferably 9.0 to 11.0 (10.0±1.0) % (w/v). In one embodiment, the internal solution of the liposome is a buffered aqueous solution isotonic or approximately isotonic (e.g., 285±50 mOsm/L) to human body fluid (plasma) having a pH of 5.8 to 6.8 (6.3±0.5) containing maltose, L-histidine and L-histidine hydrochloride, wherein the maltose concentration is preferably 9.0 to 11.0 (10.0±1.0) % (w/v).

The liposome preparation of the present invention can be prepared using known liposome production techniques. For example, methods described in Liposome Technology, vol. 1, 2nd edition (by Gregory Gregoriadis (CRC Press, Boca Raton, Ann Arbor, London, Tokyo), Chapter 4, pp 67-80, Chapter 10, pp 167-184 and Chapter 17, PP 261-276 (1993)) or the like. More specifically, sonication, ethanol injection, a French press method, ether injection, a cholic acid method, calcium fusion, a freezing and thawing method, reverse phase evaporation method or the like may be exemplified but are not limited to. The in-line liposome production techniques described in WO 2016/024510, WO 2019/088193, or the like can be used to continuously prepare the population of liposomes of the present invention in a closed tubule.

From the viewpoint of producing a population of liposomes homogeneous in their particle size, the liposome preparation of the present invention is preferably produced according to the method described in WO 2019/088193. The present invention also provides a such method for producing the liposome preparation of the present invention.

The production method of the present invention comprises, for example, the following steps.

A) preparing a primary diluting solution by mixing a first solution comprising a CD1d ligand (e.g., KRN7000), a lipid and an alcohol with a second solution comprising water in a first mixing region;
B) supplying the primary diluting solution from the first mixing region to a second mixing region through a liquid supplying tube in a predetermined time;
C) preparing a secondary diluting solution by mixing the primary diluting solution with a third solution comprising water in the second mixing region;

D) supplying the secondary diluting solution from the second mixing region to a third mixing region through a liquid supplying tube in a predetermined time; and E) preparing a tertiary diluting solution by mixing the secondary diluting solution with a fourth solution comprising water in the third mixing region.

An average particle size of a population of liposomes to be prepared is controlled within the desired range (typically, the average particle size is 90 to 110 nm and the polydispersity index (PdI) of the particle size distribution is 0.2 or less) by adjusting at least one condition selected from the group consisting of a concentration of the alcohol in the primary diluting solution, a concentration of the lipid, the predetermined time, and a temperature upon the mixing.

In one embodiment, the production method comprises a step of dissolving a CD1d ligand (e.g., KRN7000) and a lipid to an alcohol in preparation of a solution comprising a CD1d ligand (e.g., KRN7000), a lipid, and an alcohol. The heating may be applied during the dissolution process.

The average particle size of the population of liposomes can be adjusted by adjusting at least one of a concentration of alcohol in a primary diluting solution, concentration of a lipid, predetermined time for supplying a solution, and temperature upon mixing. The average particle size of the population of liposomes can be finely adjusted by serially adjusting the alcohol concentration. A population of liposomes with a desired average particle size can be manufactured by serially adjusting the alcohol concentration and then supplying a solution in a predetermined time, and in doing so, the particle size distribution that is narrow to the extent that it is acceptable at a pharmaceutical level can be achieved. Furthermore, the average particle size of the population of liposomes can be adjusted more finely by adjusting the temperature upon mixing.

As a lipid contained in the first solution, those listed above as a component other than a CD1d ligand compound that forms a liposome constituting the population of liposomes contained in the liposome preparation of the present invention can be used. In one embodiment, the lipids in the first solution comprise DOPC, DOPG-Na, DPPC, DPPG-Na and Cho. In one embodiment, the lipids in the first solution consist of DOPC, DOPG-Na, DPPC, DPPG-Na, and Cho. When the first solution contains DOPC, DOPG-Na, DPPC, DPPG-Na and Cho, the composition ratio is not particularly limited, but the molar ratio of DOPC:DOPG-Na:DPPC:DPPG-Na:Cho is preferably 15±6:15±6:15 6:15 6:40±16, more preferably 15±3:15±3:15±3:15±3:40±8, and further preferably 15±1.5:15 1.5:15±1.5:15±1.5:40±4.

The content (weight) of a CD1d ligand compound (e.g., KRN7000) in the first solution may be, for example, 1 to 21% (w/w), preferably 5 to 15% (w/w), more preferably 7 to 13% (w/w), further preferably 9 to 11% (w/w) (10±1% (w/w)) of the total weight of the components (i.e., lipids) other than the CD1d ligand compound (e.g., KRN7000) that form the liposomes.

In one embodiment, the first solution contains a CD1d ligand compound (e.g., KRN7000), DOPC, DOPG-Na, DPPC, DPPG-Na and Cho as components other than alcohol. In one embodiment, the components of the first solution other than alcohol consist of a CD1d ligand compound (e.g., KRN7000), DOPC, DOPG-Na, DPPC, DPPG-Na, and Cho. In these embodiments, the relative content (by weight) of each component is preferably as followings.

a CD1d ligand compound (e.g., KRN7000): 5.0±0.5

DOPC: 9.6±2.4

DOPG-Na: 9.7±2.4

DPPC: 9.0±2.3

DPPG-Na: 9±12.3

Cho: 12.6±3.2

An alcohol contained in a first solution comprises a monovalent or divalent alcohol comprising 1 to 6 carbon atoms. Alternatively, an alcohol contained in a first solution comprises a monovalent or divalent alcohol. In another embodiment, an alcohol contained in a first solution comprises a monovalent alcohol. In a specific embodiment, an alcohol contained in a first solution comprises a monovalent alcohol comprising 1 to 3 carbon atoms. In a specific embodiment, an alcohol contained in a first solution comprises methanol, ethanol, isopropyl alcohol, or a combination thereof. Preferably, an alcohol contained in a first solution is ethanol.

In one embodiment, a second solution and/or third solution may comprise an alcohol contained in the first solution at a lower concentration than in the first solution.

Solutions used in the production method of the present invention, including the first solution, second solution, and third solution, may comprise a solvent other than water and alcohol. Examples of such solvents are as described in WO 2019/088193.

Any solution used in the production method of the present invention, including the first solution, second solution, and third solution, may comprise an additive as needed, such as an osmotic pressure regulator, stabilizer, antioxidant, or pH adjuster. Examples of additives such as an osmotic pressure regulator, stabilizer, antioxidant, and pH adjuster are as described above.

Preferably, a second solution and a third solution are a buffered aqueous solution. A second solution and a third solution preferably comprise an osmotic pressure regulator and a pH adjuster. The osmotic pressure regulator is preferably sucrose. The pH adjuster is preferably L-histidine and hydrochloride salt thereof. The second and third solutions are preferably adjusted to be isotonic or approximately isotonic (e.g., 285±50 mOsm/L) with human body fluid (plasma). When sucrose is used as an osmotic pressure regulator, the sucrose concentration in the internal solution of liposomes is, for example, about 9.0 to 11.0 (10.0±1.0) % (w/v). When maltose is used as the osmotic pressure regulator, the maltose concentration of the internal solution of the liposome is, for example, about 9.0 to 11.0 (10.0±1.0) % (w/v). In one embodiment, the second and third solutions are a buffered aqueous solution that are isotonic or approximately isotonic (e.g., 285±50 m Osm/L) to human body fluid (plasma) containing sucrose, L-histidine and L-histidine hydrochloride, and the sucrose concentration is preferably 9.0 to 11.0 (10.0±1.0) % (w/v). In one embodiment, the second and third solutions are a buffered aqueous solution that are isotonic or approximately isotonic (e.g., 285±50 mOsm/L) to human body fluid (plasma) containing maltose, L-histidine and L-histidine hydrochloride, and the maltose concentration is preferably 9.0 to 11.0 (10.0±1.0) % (w/v). In one embodiment, the pH of the second and third solutions is, for example, 5.3 to 7.3 (6.3±1.0), preferably 5.8 to 6.8 (6.3±0.5). In one embodiment, the pH of any solution comprising water used in the production method of the present invention, including the first, second and third solutions, is for example 5.3 to 7.3 (6.3±1.0), preferably 5.8 to 6.8 (6.3±0.5). In this manner, the pH of the finally obtained suspension of the population of liposomes of the present invention or the internal solution of liposomes can be adjusted to, for example, 5.3 to 7.3 (6.3±1.0), preferably 5.8 to 6.8 (6.3±0.5).

The average particle size of the population of liposomes changes over time if the alcohol concentration (wt %) in a primary diluting solution is adjusted to a specific value (also referred to as a "fluidity changing point" herein) or higher, whereas the particle size of the liposomes hardly changes at an alcohol concentration less than the fluidity changing point. In one embodiment, the fluidity changing point may change depending on the composition of liposomes, temperature, and pressure. In one embodiment, the fluidity changing point may change depending on the type of alcohol in the primary diluting solution. In one embodiment, the fluidity changing point may change depending on the composition of liposomes, temperature, and pressure. In one embodiment, the fluidity changing point does not change depending on the composition of liposomes and/or presence/absence of drug loaded in liposomes if the type of alcohol in the primary diluting solution is the same.

In one embodiment, in the step of supplying the primary diluting solution from the first mixing region to a second mixing region through a liquid supplying tube in a predetermined time, the alcohol concentration and temperature are adjusted so that the alcohol concentration in the primary diluting solution is to be the fluidity changing point or higher. For example, the liquid supplying tube is heated to 85±5° C. In addition, in the step of supplying the secondary diluting solution from the second mixing region to a third mixing region through a liquid supplying tube in a predetermined time, the alcohol concentration and temperature are adjusted so that the alcohol concentration in the secondary diluting solution is below or equal to the fluidity changing point or below the fluidity changing point. For example, the liquid supplying tube is set at 20±5° C. That is, the step of supplying the primary diluting solution from the first mixing region to a second mixing region through a liquid supplying tube in a predetermined time is performed at the phase transition temperature of the lipids in the primary diluting solution or higher, and the step of supplying the secondary diluting solution from the second mixing region to a third mixing region through a liquid supplying tube in a predetermined time is performed at a temperature below the phase transition temperature of the secondary diluting solution. By controlling the reaction conditions in this way, liposomes or a membrane thereof is destabilized in the primary diluting solution, and the fluidity of lipid increases by heating the lipid to the phase transition temperature or higher. Thus, the frequency of fusing upon contact with one another due to Brownian motion increases. For this reason, fusion between liposomes generated with passage of time proceeds uniformly so that the particle size increases while maintaining a certain granularity distribution. On the other hand, by adjusting the alcohol concentration in the secondary diluting solution to less than the fluidity changing point, the particle size distribution of liposomes controlled in the primary diluting solution is fixed so that the value does not change.

A stainless-steel capillary tube (SSCT) can be used as a liquid supplying tube in Process B and Process D. The reaction liquids can be mixed in an inline mixer.

In one embodiment, the average particle size of the population of liposomes may be controlled to the desired range described above (typically, average particle size is 90 to 110 nm and the polydispersity index (PdI) of the particle size distribution is 0.2 or less) by adjusting the predetermined time (time of retention) for the primary diluting solution to reach the second mixing region from the first mixing region (in some cases, predetermined time for the secondary diluting solution to reach the third mixing region from the second mixing region). In one embodiment, the predetermined time the primary diluting solution is retained in a liquid supplying tube until reaching the second mixing region from the first mixing region (in some cases, time the secondary diluting solution is retained in a liquid supplying tube until reaching the third mixing region from the second mixing region) is controlled with at least one of length of a flow channel length and flow rate between mixing regions. In one embodiment, the predetermined time the primary diluting solution is retained in a liquid supplying tube until reaching the second mixing region from the first mixing region is controlled with the flow rate between the first mixing region and the second mixing region.

In addition, the average particle size of the population of liposomes can be controlled within the desired range (typically, the average particle size is 90 to 110 nm and the polydispersity index (PdI) of the particle size distribution is 0.2 or less) by controlling the temperature, lipid concentration in the primary diluting solution, pressure, or the like in each step of the production method of the present invention.

In one embodiment, the production method of the present invention comprises adjusting the composition of a solution after producing the population of liposomes. In one embodiment, the production method the present invention comprises adjusting the liposome concentration after producing the population of liposomes. The step of adjusting the composition of a solution and the step of adjusting the liposome concentration can be performed simultaneously or separately. For example, the step of adjusting the composition of a solution and the step of adjusting the liposome concentration can be performed simultaneously by using a hollow fiber membrane column disclosed in WO 2016/024510. Examples of means for adjusting the liposome concentration in a solution comprising the produced population of liposomes and adjusting the composition of a solution include, but are not limited to, ultrafiltration, dialysis, and the like. For example, in this process, the pH of the solution containing the produced population of liposomes (liposome suspension) is adjusted to 5.3 to 7.3 (6.3±1.0), preferably 5.8 to 6.8 (6.3±0.5).

In one embodiment, the surface of liposomes constituting the population of liposomes contained in the liposome preparation of the present invention may be modified with a modifier. Examples of modifiers include, but are not limited to, polyethylene glycol (PEG), ficoll, polyvinyl alcohol, styrene-maleic anhydride alternating copolymer, divinyl ether-maleic anhydride alternating copolymer, polyvinylpyrrolidone, polyvinyl methyl ether, polyvinyl methyl oxazoline, polyethyl oxazoline, polyhydroxypropyl oxazoline, polyhydroxypropyl methacrylamide, polymethacrylamide, polydimethylacrylamide, polyhydroxypropyl methacrylate, polyhydroxyethyl acrylate, hydroxymethyl cellulose, hydroxyethyl cellulose, polyaspartamide, synthetic polyamino acid, derivatives thereof, and the like. Liposomes may be more likely to remain in blood for a long period of time by modification with PEG or a PEG derivative. Liposomes may be more likely to reach a target tissue by modifying the liposomes with a targeting molecule (e.g., antibody) having affinity for a specific tissue. In one embodiment, the surface of liposomes constituting the population of liposomes contained in the liposome preparation of the present invention may not be modified with a modifier.

In one embodiment, the liposome preparation of the present invention is stable and the average particle size of the population of liposomes contained in the preparation is maintained at 90 to 110 nm (preferably 92.9 to 101.0 nm, 93.1 to 101.0 nm, 93.5 to 101.0 nm, 94.6 to 101.0 nm, 95.7 to 101.0 nm, 95.8 to 101.0 nm, 95.9 to 101.0 nm) for at least 1 month (e.g., 2 months or more, 3 months or more, or 6 months or more) at a temperature of 25° C. and a relative humidity of 60% RH (accelerated test conditions).

The liposome preparation of the present invention may be provided in any form, for example, as a liposome suspension in which the population of liposomes is suspended in an aqueous solvent (i.e., suspension), or as a lyophilized solid state (i.e., lyophilized preparation).

In one embodiment, the population of liposomes is contained in the liposome preparation of the present invention as a liposome suspension. That is, the liposome preparation of the present invention may be provided as a suspension preparation (referred to as the liposome suspension preparation of the present invention). The liposome suspension preparation of the present invention includes the liposome suspension preparation of the present invention. The liposome suspension preparation of the present invention contains the aforementioned population of liposomes suspended in an aqueous solvent. The liposome suspension preparation of the present invention is suitably used for administering a population of liposomes containing a CD1d ligand to a subject including a human by injection. Examples of aqueous solvents include water and mixtures of water and water-soluble organic solvents, although they are not particularly limited. Water-soluble organic solvents include, without limitation, an alcohol. The alcohol is preferably a monovalent or divalent alcohol comprising 1 to 6 (preferably 1 to 3) carbon atoms. Examples of alcohol include methanol, ethanol, isopropyl alcohol, or combinations thereof. The alcohol is preferably ethanol. The aqueous solvent is preferably water.

The aqueous solvent may contain a pharmaceutically acceptable additive Such as an osmotic pressure regulator, stabilizer, antioxidant, and pH adjuster, as needed.

An osmotic pressure regulator is not particularly limited. Examples thereof include inorganic salts such as sodium chloride, potassium chloride, sodium hydrogen phosphate, sodium dihydrogen phosphate, and potassium dihydrogen phosphate, polyols such as glycerol, mannitol, and sorbitol, and saccharides such as glucose, fructose, lactose, maltose, and sucrose.

A stabilizer is not particularly limited. Examples thereof include saccharides such as glycerol, mannitol, sorbitol, lactose, and sucrose, and sterols such as cholesterol.

An antioxidant is not particularly limited, Examples thereof include ascorbic acid, uric acid, and tocopherol homologs (e.g., vitamin E). While tocopherol has 4 isomers α, β, γ, and δ, any of them can be used in the present invention.

A pH adjuster can be any basic or acidic compound. Examples thereof include sodium hydroxide, citric acid, acetic acid, triethanolamine, sodium hydrogen phosphate, sodium dihydrogen phosphate, L-histidine and hydrochloride salt thereof, and the like.

The aqueous solvent is preferably a buffered aqueous solution containing an osmotic pressure regulator and a pH adjuster. The osmotic pressure regulator is preferably sucrose or maltose, and more preferably sucrose. The pH adjuster is preferably L-histidine and hydrochloride salt thereof.

In addition to the additives described above, an analgesic agent, preservative, and other additives may be added to the aqueous solvent as needed.

Examples of analgesic agents include glucose, benzyl alcohol, mepivacaine hydrochloride, xylocaine hydrochloride, procaine hydrochloride, carbocaine hydrochloride, or the like.

Examples of preservatives include paraoxybenzoates, chlorobutanol, benzyl alcohol, phenethyl alcohol, dehydroacetic acid, sorbic acid, or the like.

When lyophilizing the liposome suspension preparation of the present invention to prepare a lyophilized preparation, it is preferable to add a cryoprotectant to the aqueous solvent to prevent aggregation or fusion of liposomes or collapse of the lipid membrane. Examples of cryoprotectants include sugars such as lactose, glucose, mannose, maltose, galactose, fructose, sorbose, raffinose, neuraminic acid, glucosamine, galactosamine, N-methylglucosamine, mannitol, sorbitol, trehalose and sucrose, amino acids such as glycine, alanine, lysine, and arginine, glycerin, polyethylene glycol, polyvinylpyrrolidone, dextran, or the like.

The aqueous solvent preferably contains a sugar such as sucrose, since sucrose and other sugars have various functions including an osmotic pressure regulator, stabilizers, and cryoprotectant as one ingredient.

The aqueous solvent (i.e., liposome suspension) may be preferably adjusted to be isotonic or approximately isotonic (e.g., 285±100 mOsm/L) with human body fluid (plasma). When sucrose is used as an osmotic pressure regulator, the sucrose concentration in the aqueous solvent may be preferably about 9.0 to 11.0 (10.0±1.0) % (w/v).

The pH of the aqueous solvent (i.e., liposome suspension) is adjusted to, for example, 5.3 to 7.3 (6.3±1.0), preferably 5.8 to 6.8 (6.3±0.5). In one embodiment, the aqueous solvent is a buffered aqueous solution isotonic or approximately isotonic (e.g., 285±50 m Osm/L) to human body fluid (plasma) having pH of 5.8 to 6.8 (6.3±0.5) containing sucrose, L-histidine and L-histidine hydrochloride, and the sucrose concentration is preferably 9.0 to 11.0 (10.0±1.0) % (w/v). As an example, the theoretical value of the osmotic pressure of a buffered aqueous solution containing L-histidine (15 mM), L-histidine hydrochloride (5 mM) and sucrose (10.0% (w/v)) is 311.6 mOsm/L.

The content of liposomes containing a CD1d ligand compound in the liposome suspension preparation of the present invention is not particularly limited, but may range, for example, from 0.01 to 100 mg/ml, preferably from 0.5 to 50 mg/ml, preferably 1.0 to 10 mg/ml (e.g., 4.5 to 5.5 (5.0±0.5) mg/ml) as a concentration of a CD1d ligand compound (e.g., KRN7000).

In one embodiment, the population of liposomes is contained in the liposome preparation of the present invention as a lyophilized product. That is, the liposome preparation of the present invention may be provided as a lyophilized preparation (referred to as the liposome lyophilized preparation of the present invention). The lyophilized product of the present invention can be obtained by subjecting the above-described population of liposomes suspended in an aqueous solvent (i.e., the liposome suspension preparation of the present invention described above) to a lyophilization process.

For example, the liposome suspension of the present invention may be divided into small portions and filled into vials or other containers and then frozen at a temperature of −20 to −80° C. to obtain a frozen composition, which can then be subjected to a reduced pressure condition (e.g., 10 Pa or below) to sublimate water to obtain the liposome lyophilized preparation of the present invention. In order to prevent aggregation or fusion of liposomes or collapse of lipid membranes during lyophilization, it is preferable to add the above-mentioned cryoprotectant to the liposome suspension.

By dispersing the liposome lyophilized preparation of the present invention with an aqueous solvent (e.g., water), the liposome suspension preparation of the present invention that meets the above conditions can be reconstituted. The reconstituted liposome suspension preparation of the present invention is provided for administration.

In this specification, the particle size and the polydispersity index of the particle size distribution of a population of liposomes contained in a lyophilized preparation means the particle size and the polydispersity index of the particle size distribution of a population of liposomes contained in a suspension preparation obtained by dispersing the lyophilized preparation with an aqueous solvent (e.g., water) to reconstitute it.

The liposome preparation of the present invention can be administered either orally or parenterally, but it is especially suitable for injection because it has improved in vivo pharmacokinetics when administered by injection, and the maximum blood concentration of the CD1d ligand compound (e.g., KRN7000) is increased and the blood half-life is extended as compared to conventional preparations. The liposome preparation of the present invention can be used for, for example, intravenous, intramuscular, intradermal, subcutaneous, or intra-organic injection administration, preferably for intravenous injection administration.

When the liposome preparation of the present invention is used as a preparation for injection administration, it can be stored and used in a form filled in a container. The container is preferably a sealed container. As the form of the sealed container, an ampoule, vial, bag, or the like can be mentioned. As the material of the container, glass, plastic, or the like can be mentioned. When the liposome preparation of the present invention is filled into a container such as an ampoule or vial, the gas phase portion of the container space may be replaced with an inert gas. Nitrogen is a good example of an inert gas. For example, each container is filled with one injectable dose of liposomes containing a CD1d ligand compound (e.g., KRN7000). For example, when KRN7000 is used as a CD1d ligand compound, the liposome preparation of the present invention is filled into a container so that each container contains 0.5 to 100 mg (e.g., 5.0±0.5 mg, 11.5±0.5 mg) of KRN7000.

The liposome preparation of the present invention has improved in vivo pharmacokinetics, and the maximum blood concentration of a CD1d ligand compound (e.g., KRN7000) is increased and its blood half-life is extended as compared to that of conventional preparations. In addition, since the liposome preparation of the present invention has a high ability to induce IL-4 and a low ability to induce IFN-γ, and can effectively induce Tregs, it is expected to have an excellent immunosuppressive or immune tolerance inducing effect. Therefore, the liposome preparation of the present invention is useful for prevention or treatment of graft-versus-host disease (GVHD), organ transplant rejection, autoimmune diseases, or the like. Autoimmune diseases include, but are not limited to, systemic lupus erythematosus, scleroderma, polyarteritis, myasthenia gravis, multiple sclerosis, autoimmune thyroiditis, type 1 diabetes, rheumatoid arthritis, Sjogren's syndrome, ANCA-related vasculitis, Takayasu disease, Behçet's disease, adult still disease, relapsing polychondritis, IgA vasculitis, polymyalgia rheumatica, antiphospholipid antibody syndrome, ankylosing spondylitis, Kawasaki disease, Crohn's disease, ulcerative colitis, psoriasis vulgaris, pemphigoid, primary biliary cirrhosis, primary sclerosing cholangitis, idiopathic interstitial pneumonia, or the like.

By administering an effective amount of the liposome preparation of the present invention to a subject (e.g., human) in need thereof, the development of GVHD, organ transplant rejection, an autoimmune disease, or the like in said subject can be prevented, or GVHD, organ transplant rejection, an autoimmune disease, or the like in said subject can be treated. In the case of preventing or treating GVHD, the subject in need of these preparations include a person who has already received transplantation of allogeneic tissue (bone marrow, blood, or the like) or cells (hematopoietic stem cell, or the like) and is at high risk of developing GVHD in the future, although the person does not currently develop GVHD, a person who has already received transplantation of allogeneic tissue (bone marrow, blood, or the like) or cells (hematopoietic stem cell, or the like) and have developed GVHD, a person scheduled to receive a transplant of allogenic tissue (bone marrow, blood, or the like) or cells (hematopoietic stem cells, or the like), or the like. In the case of preventing or treating organ transplant rejection, the subject in need of these preparations include a person who has already received a transplant of an allogeneic or xenogeneic tissue or cell and is at high risk of developing rejection in the future, although the person does not currently develop rejection, a person who has already received a transplant of an allogeneic or xenogeneic tissue or cell and have developed rejection, a person scheduled to receive a transplant of an allogeneic or xenogeneic tissue or cell, or the like. The present invention provides a liposome preparation of the present invention for use in the prevention or treatment of GVHD, organ transplant rejection, autoimmune disease, or the like. In one embodiment, GVHD may be caused by allogeneic hematopoietic stem cell transplantation.

As used herein, the term "effective amount" means an amount which results in an aimed effect (e.g., a therapeutic effect) on the subject, and means, for example, that in the subject who has received the amount, the symptom of the disease or condition is alleviated, mitigated, deleted, or the development of the symptom of the disease or condition is delayed or suppressed compared with a subject who has not received the amount. An effective amount can be appropriately determined by a doctor in view of the age, weight, sex and the severity of the disease or the like of the subject.

As used herein, "prevention" means, with respect to a disease or disorder (e.g., GVHD, organ transplant rejection), to prevent such a condition before it occurs, to reduce the risk of such a condition occurring, or to mitigate or reduce such a condition.

All references cited in the present specification, including publication, patent document and the like, are hereby incorporated individually and specifically by reference, to the extent that the entireties thereof have been specifically disclosed herein.

The present invention is explained in more detail in the following by referring to Examples, which are not to be construed as limitative.

EXAMPLES

[Experimental Example 1] Production and Stability Evaluation of a Comparative Preparation (Hereinafter Referred to as RGI-2001-001)

The manufacturing process for RGI-2001-001 is described below.

Step 1: RGI-2001-001 Intermediate (Lyophilized Product of KRN7000/Lipid Mixture)

Step 1a) Preparation of 90% (w/w) Tert-Butanol Solution

Water for injection was placed in a beaker and heated to 55 to 60° C. Tert-butanol was dissolved on a hot plate with stirring. Tert-butanol was poured into a pyrogen-free glass container (Pyrex), added with water for injection to achieve a final concentration of 90% (weight/weight), and stirred for 10±5 min while heating to 55 to 60° C.

Step 1b) Dissolution of Lipid Mixture

To a lipid mixture containing the following lipids (molar ratio 15:15:15:15:40);

1,2-dioleoyl-sn-glycero-3-phosphocholine (DOPC), 1,2-dioleoyl-sn-glycero-3-[phospho-rac-(1-glycerol)] sodium salt (DOPG-Na), 1,2-dipalmitoyl-sn-glycero-3-phosphocholine (DPPC), 1,2-dipalmitoyl-sn-glycero-3-[phospho-rac-(1-glycerol)] sodium salt (DPPG-Na), and cholesterol, tert-butanol was added to a final concentration of 100 g/L and stirred at 45±5° C. until clear.

Step 1c) Preparation of KRN7000/Cyclohexane Solution

A powder of KRN7000 ((2S,3S,4R)-1-o-(α-D-galactopyranosyl)-2-(N-hexacosanoylamino)-1,3,4-octadecanetriol) (REGiMMUNE) was weighted in a pyrogen-free glass vessel (Pyrex) and added with cyclohexane to reach a final concentration of 10 g/L. The solution was stirred at 47±1° C. for 20±5 min.

Step 1d) Preparation of KRN7000/Lipid Mixture Solution

The lipid mixture solution was added to the KRN7000/cyclohexane solution and stirred at 47±1° C. until clear to give a KRN7000/lipid mixture solution.

Step 1e) Lyophilization

A glass container containing the KRN7000/lipid mixture solution was carefully rotated in a dry ice/acetone bath to uniformly freeze the mixture on the inner wall of the container. After freezing, the glass container was allowed to stand on dry ice for at least 1 hour (within a maximum of 24 hours). The glass container containing the frozen KRN7000/lipid mixture was placed in a lyophilizer and the following process was proceeded.

The product was frozen for at least 2±0.5 hours after the temperature sensor in the product reached −40° C. or below.

After freezing was completed, the temperature of the frozen product was maintained at −40° C. or below.

The degree of vacuum was set to 250 micron or less.

The shelf temperature was increased from −40° C. or below to −35±3° C. over a period of 6±0.5 hours or more.

The shelf temperature was maintained at −35±3'C for 12±0.5 hours.

The shelf temperature was increased from −35±3° C. to 25±3° C. over a period of 4±0.5 hours.

The temperature sensor of the product was maintained at 25±3° C. for 12±0.5 hours until the solenoid-type bleed valve was disabled.

Once the maximum vacuum was reached, the product was maintained at 25±3° C. for a minimum of 83 hours.

As soon as lyophilization was completed and the chamber pressure reached atmospheric pressure, the glass container containing the product was sealed with a cap and stored at −20° C.

If the total weight of the lyophilized product was 102% or more of the total weight of the KRN7000/lipid mixture, the product was further lyophilized at 25±3° C. for 24 hours.

Step 2: Production of RGI-2001-001 API

Step 2a) Preparation of Buffer Solution for Formulation

The water for injection was added with sucrose to a final concentration of 10%, L-histidine to a final concentration of 15 mM, and L-histidine hydrochloride hydrate to a final concentration of 5 mM, then stirred for 15 minutes to adjust the final pH to 6.5±0.2. The resulting buffer solution was passed through a sterile filter (pore size 0.2 μm) before the next step.

Step 2b) Hydration of RGI-2001-001 Intermediate

The RGI-2001-001 intermediate (KRN7000/lipid mixture), which had been stored in a frozen state, was brought to room temperature for 30 minutes. The amount of buffer for preparation to be used was calculated from the buffer density (1.04 g/mL) and the final solution density (0.055 g/mL). The buffer for preparation was added under aseptic conditions to the glass container containing RGI-2001-001 intermediate and stirred at 30-45° C. for approximately 60 minutes until completely hydrated.

Step 2c) High-Pressure Extrusion

The hydrated RGI-2001-001 intermediate solution was passed through an extruder equipped with a polycarbonate membrane filter (pore size 0.2 μm) five times at a target pressure of 200-300 psi (not exceed 600 psi) under aseptic conditions. The obtained filtrate was then passed through an extruder equipped with a polycarbonate membrane filter (pore size 0.1 μm) once. As a final step, the obtained filtrate was passed through an extruder equipped with two polycarbonate membrane filters (pore size 0.1 μm) 10 times. The final recovered product was passed through a sterile filter (pore size 0.2 μm) and stored at 2 to 8° C. as a RGI-2001-001 API.

The results of the RGI-2001-001 accelerated (25° C.) test are listed in the following table.

TABLE 1

| RGI-2001 Drug Product<br>Strage Conditions: 25 ± 2° C., 60 ± 5% Relative Humidity, Inverted | | | | | | | |
|---|---|---|---|---|---|---|---|
| Test | Specification | | 0 M | 1 M | 2 M | 3 M | 6 M |
| Appearance | Opaque suspension, white to pale yellowish liquid | | Opaque suspension, white | Opaque suspension, white liquid | Opaque suspension, white liquid | Opaque suspension, white liquid | Opaque Suspension, white liquid |
| pH | 6.8 ± 0.5 | | 6.8 | 6.6 | 6.6 | 6.6 | 6.8 |
| Osmolality | Report value | | 369 mOsm/Kg | 348 mOsm/Kg | 359 mOsm/Kg | 349 mOsm/Kg | 366 mOsm/Kg |
| Content by HPLC | KRN7000 | 5.0 ± 0.5 mg/mL | 4.8 mg/mL | 4.7 mg/mL | 4.7 mg/mL | 4.8 mg/mL | 4.6 mg/mL |
| | Cholesterol | 12.6 ± 3.2 mg/mL | 12.3 mg/mL | 12.3 mg/mL | 12.7 mg/mL | 11.6 mg/mL | 11.5 mg/mL |

TABLE 1-continued

| RGI-2001 Drug Product<br>Strage Conditions: 25 ± 2° C., 60 ± 5% Relative Humidity, Inverted | | | | | | | |
|---|---|---|---|---|---|---|---|
| Test | | Specification | 0 M | 1 M | 2 M | 3 M | 6 M |
| | DOPC | 9.6 ± 2.4 mg/mL | 8.2 mg/mL | 8.6 mg/mL | 8.4 mg/mL | 7.5 mg/mL | 7.4 mg/mL |
| | DPPC | 9.0 ± 2.3 mg/mL | 8.5 mg/mL | 8.5 mg/mL | 8.7 mg/mL | 7.9 mg/mL | 7.2 mg/mL |
| | DPPG-Na | 9.1 ± 2.3 mg/mL | 8.9 mg/mL | 8.7 mg/mL | 8.6 mg/mL | 8.2 mg/mL | 7.7 mg/mL |
| | DOPG-Na | 9.7 ± 2.4 mg/mL | 8.7 mg/mL | 8.7 mg/mL | 8.4 mg/mL | 7.7 mg/mL | 6.9 mg/mL |
| Drug | KRN7000 | Report value | N/A | 10.9% | 10.9% | 10.8% | 11.1% |
| Product | Cholesterol | Report value | Not reported | 80.5% | 79.7% | 77.3% | 73.1% |
| Purity | DOPC | Report value | | 1.6% | N/A | N/A | N/A |
| | DPPC | Report value | | 7.0% | 7.5% | 7.0% | 7.6% |
| | Unknown | Report value | No impurities detected | No impurities detected | 1.9% (RRT 0.32) | 4.9% (RRT 0.32) | 5.9% (RRT 0.32)<br>0.9% (RRT 0.36) |
| Particle | Mean | 110 ± 30 nm | 124 ± 4 nm | 118 nm | 120 nm | 122 nm | 121 nm |
| Size | <50 nm | NMT 10% | <1% | 1% | 1% | 1% | 1% |
| | >450 nm | NMT 10% | <1% | 0% | 0% | 0% | 0% |

The average particle size of RGI-2001-001 was 124 nm immediately after manufacture and remained around 120 nm during the subsequent 6-month accelerated test period. Furthermore, the DOPG-Na content after 6 months was out of the specification. These results suggest that the average particle size of the comparative formulation (RGI-2001-001) is uniform and stable at around 120 nm.

[Experimental Example 2] Production Method and Stability Evaluation of the Example Formulation (Hereinafter Referred to as RGI-2001-003)

The manufacturing process for RGI-2001-003 is described below.

Step 1) Preparation of Buffer Solution for Formulation

Sucrose, L-histidine, L-histidine hydrochloride hydrate and water for injection were added to a single-use sterile bag and the mixture was completely dissolved at room temperature. Water for injection was added to achieve a final sucrose concentration (w/v) of 10% and a final sucrose density of 1.038 g/mL, and then the mixture was passed through a sterile filter (pore size 0.2 μm) and collected in a sterile plastic container.

Step 2a) Dissolution of RGI-7000 and Lipids

KRN7000 (REGiMMUNE) (final concentration 5 mg/mL), 1,2-dioleoyl-sn-glycero-3-phosphocholine (DOPC) (final concentration 15 mol %), 1,2-dioleoyl-sn-glycero-3-[phospho-rac-(1-glycerol)] sodium salt (DOPG-Na) (final concentration 15 mol %)

1,2-dipalmitoyl-sn-glycero-3-phosphocholine (DPPC) (final concentration 15 mol %)

1,2-dipalmitoyl-sn-glycero-3-[phospho-rac-(1-glycerol)] sodium salt (DPPG-Na) (final concentration 15 mol %), and cholesterol (final concentration 40 mol %)

was added to ethanol, dissolved at 85±5'° C., and sonication treatment was continued until the solution became clear.

Step 2b) Preparation of RGI-2001-003 API Solution

The ethanol solution containing KRN7000 and lipids and the buffer solution for formulation were passed through a stainless-steel capillary tube (SSCT) set at 85±5° C. and mixed in an inline mixer to obtain the crude product of the RGI-2001-003 API solution. The crude product was mixed with the buffer solution for formulation in a separate inline mixer and then cooled by passing through an SSCT set at 20±5° C. The liposome particle size of RGI-2001-003 API was finely adjusted to average particle size of approximately 100 nm by changing the pump speed.

Step 2c) Concentration and Diafiltration

The RGI-2001-003 API was concentrated to 60% with a polyethersulfone resin hollow fiber membrane module (excluding less than 500 kDa) and diafiltrated with 10-fold weight of the buffer solution for formulation.

Step 2d) Adjustment of RGI-2001-003 API Concentration

The weight of KRN7000 content in RGI-2001-003 API was confirmed by high-performance liquid chromatography, and the final concentration was adjusted to 5.0±0.5 mg/mL by dilution with water for injection and concentration by diafiltration. The average particle size was adjusted to approximately 100 nm by dynamic light scattering.

Step 2e) Sterilization of RGI-2001-003 API

The product was collected in a sterile plastic bag through a sterile filter (0.2 μm). RGI-2001-003 API was stored refrigerated (5±3° C.) under light shielding until vial filling.

The results of the RGI-2001-003 accelerated (25° C.) test are listed in the following table.

TABLE 2

| 1. Test Conditions | |
|---|---|
| Sample storage form | Nude vials Inverted storage |
| Sample storage conditions | Temperature: 25 ± 2° C.<br>Relative Humidity: 60 ± 5% RH |
| Sample storage location | 25° C. stability test coffer No. 1 |

| 2. Test Results | | | | | | |
|---|---|---|---|---|---|---|
| Test items | Criterion | IN※ | 1 M | 2 M | 3 M | 6 M |
| Appearance | White to pale yellowish suspension | White suspension | White suspension | White suspension | White suspension | White suspension |
| pH | 6.3 ± 0.5 | 6.3 | 6.4 | 6.4 | 6.3 | 6.4 |

TABLE 2-continued

| | | | | | | | |
|---|---|---|---|---|---|---|---|
| Osmolality | | Reported value (mOsm) | 353 | 355 | 356 | 344 | 343 |
| KRN7000 content | | 5.0 ± 0.5 mg/mL | 6.4 | 5.2 | 5.3 | 5.2 | 5.1 |
| Lipid content | DOPC | 9.6 ± 2.4 mg/mL | 10.7 | 10.2 | 9.8 | 9.5 | 8.3 |
| | DOPG-Na | 9.7 ± 2.4 mg/mL | 10.5 | 10.1 | 9.7 | 9.4 | 8.1 |
| | DPPC | 9.0 ± 2.3 mg/mL | 10.0 | 9.2 | 9.1 | 9.0 | 7.8 |
| | DPPG-Na | 9.1 ± 2.3 mg/mL | 9.9 | 9.5 | 9.1 | 8.8 | 7.6 |
| | Cholesterol | 12.6 ± 3.2 mg/mL | 14.1 | 14.1 | 14.0 | 14.1 | 14.0 |
| Average particle size | | 110 ± 30 nm | 96 | 101 | 99 | 99 | 96 |
| | Less then 50 nm | 10% of total | 5 | 4 | 3 | 3 | 3 |
| | More than 450 nm | 10% of total | 0 | 0 | 0 | 0 | 0 |
| Analogous substances | each: reported | RRT 0.21 | N.D. | 0.24 | N.D. | N.D. | 0.90 |
| (Drug Product Purity) | value | RRT 0.40 | N.D. | N.D. | 0.79 | 1.24 | 2.65 |
| | | Total amount: reported value | N.D. | 0.24 | 0.79 | 1.24 | 3.55 |
| | Storaged number per time point | | — | 6 | 6 | 6 | 6 |

※IN: Results of the quality test of this product were used.

RGI-2001-003 was manufactured according to the techniques described in the Patent Documents 2 and 3 in which the liposome average particle size was set to 100 nm. The KRN7000 content and lipid composition of RGI-2001-003 are the same as those of RGI-2001-001. The average particle size was approximately 96 nm immediately after manufacture, which was very close to the set value, and remained around 100 nm until the end of accelerated test. Deviation from the specification was not observed. These results suggest that RGI-2001-003 liposome preparation has an intended average particle size (100 nm) and excellent long-term stability.

[Experimental Example 3] Analysis of Pharmacokinetics in Human Clinical Trials

In a phase I clinical trial, RGI-2001-001 was administered intravenously at a dose of 100 μg/kg as KRN7000 within 30 minutes after transplantation to six patients who had received hematopoietic stem cell transplantation. 2 mL of peripheral blood was collected before and 0.5, 1, 2, 4, 6, 8, 24, 48, 72, and 96 hours after transplantation, respectively, and plasma components were collected. KRN7000 in each plasma was separated and identified by liquid chromatography-mass spectrometry (LC-MS/MS).

Similarly, RGI-2001-003 was administered intravenously at a dose of 100 μg/kg as KRN7000 within 30 minutes after transplantation to seven patients who had received hematopoietic stem cell transplantation, and 2 mL of peripheral blood was collected before and 0.5, 2, 4, 6, 8, 24, and 48 hours after transplantation. Plasma components were collected, and plasma KRN7000 was separated and identified by LC-MS/M. These patients were treated with RGI-2001-003 at a dose of 100 μg/kg as KRN7000 intravenously once a week for 5 to 6 consecutive doses. For the administration on day 14, 2 mL of peripheral blood was collected before and 0.5 and 4 hours after administration, respectively, plasma components were collected, and plasma KRZN7000 was separated and identified by LC-MS/M. The NKT response and the number of activated Tregs (Ki-67+%) in patients treated with RGI-2001-003 administration were monitored over time.

The results showed that the maximum blood concentration (Cmax) and blood half-life (t½) were 187.6 ng/mL and 23.4 hours in the RGI-2001-001 administration group, whereas they were 881 ng/mL and 35.8 hours in the RGI-2001-003 administration group. These results indicate that the maximum blood concentration (Cmax) was significantly higher and the blood half-life (t½) was significantly longer in the RGI-2001-003 administration group compared to the RGI-2001-001 administration group (Table 3). With respect to the time-course changes in pharmacokinetics, RGI-2001-003 showed a typical decay curve, whereas RGI-2001-001 showed an irregular transition (FIG. 1). Plasma levels of KRN7000 were similar for the first and multiple administrations of RGI-2001-003. The exposure of patients to KRN7000 was similar on days 0 and 14 after repeated weekly administrations of RGI-2001-003 (Table 4, FIG. 1). RGI-2001-003 induced NKT cell responses and an increase in regulatory T cell counts (Table 5).

TABLE 3

Maximam concentration in blood (Cmax) and blood half-life (t1/2)

| | Cmax (ng/ml) | t1/2 (h) |
|---|---|---|
| RGI-2001-001 | 187.6 | 23.4 |
| RGI-2001-003 | 881 | 35.8 |

TABLE 4

| KRN7000 PK Parameters | Day 0 | Day 14 |
|---|---|---|
| $C_{max}$ (ng/ml) | 881 (42%) | 570 (63%) |
| $C_{min}$ (ng/ml) | NA | 34.1 (130%) |
| $AUC_{0-4}$ (ng*h/mL) | 3000 (48%) | 1890 (63%) |
| *Est. $AUC_{0-inf}$ (ng*h/mL) | 42500 (80%) | NA |
| $t_{1/2}$ (h) | 35.8 (40%) | NA |

TABLE 5

| Patient ID | RGI-2001 Dose 100 μg/kg weekly Total dose rec'd | NKT reaction on day 14 | Treg % in CD4 + T cells on day 14 | Activated Treg (kl-67+)% |
|---|---|---|---|---|
| 01-101 | 6 | ↑↑ | 11 | ↑ |
| 01-102 | 5 | ↑ | 12 | ↑↑↑ |
| 01-103 | 6 | ↑↑ | 11 | ↑ |
| 01-104 | 6 | ↑↑ | 19 | ↑↑↑ |
| 02-101 | 6 | ↑↑↑ | 7 | ↑ |
| 02-102 | 6 | ↑ | 8 | ↑↑ |
| 05-101 | 6 | ↑↑↑ | 4 | — |

[Experimental Example 4] Evaluation of Drug Efficacy in Mice

For RGI-2002, an action mechanism has been reported in which after intravenous administration, RGI-2001 is incorporated in splenic marginal zone B cells, releases KRN7000 intracellularly, and after KRN7000 binds to CD1d molecule, it is presented on the cell surface and induces IL-4 production by iNKT cells and induces regulatory T cells (Tregs) (Non-Patent Document 1). On the other hand, when dendritic cells incorporate RGI-2001, it works to induce IFN-γ production by iNKT cells.

Figure 2:
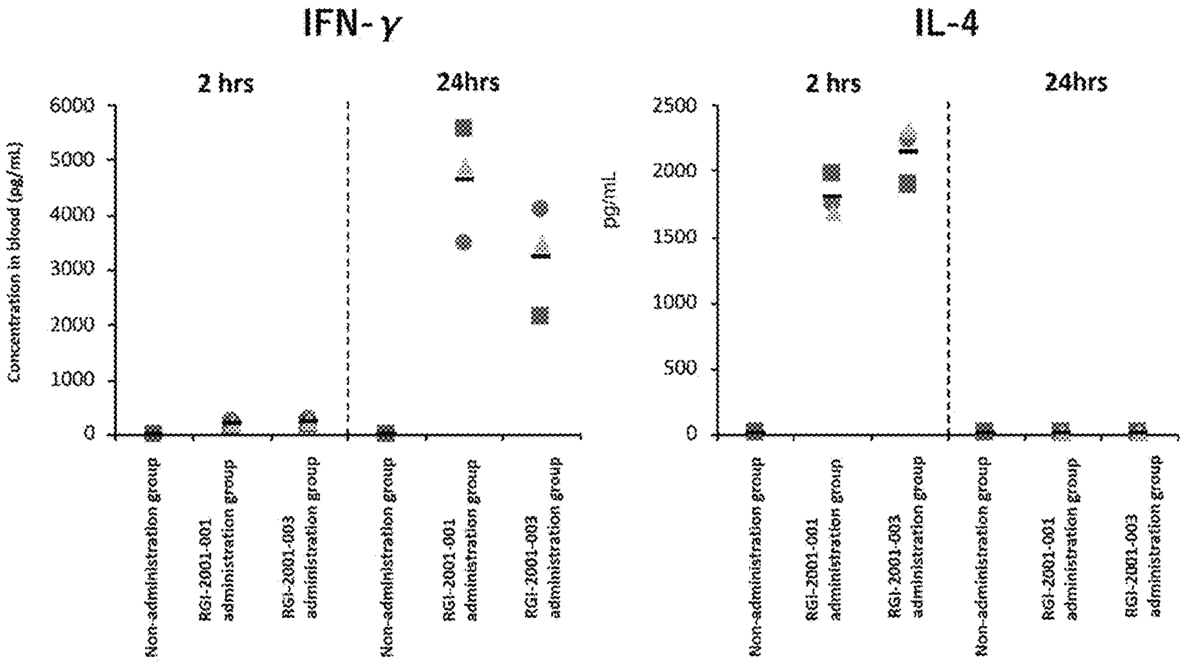
FIG. 2 shows IFN-γ and IL-4 concentrations in the blood of mice administered with RGI-2001.
Figure 3:
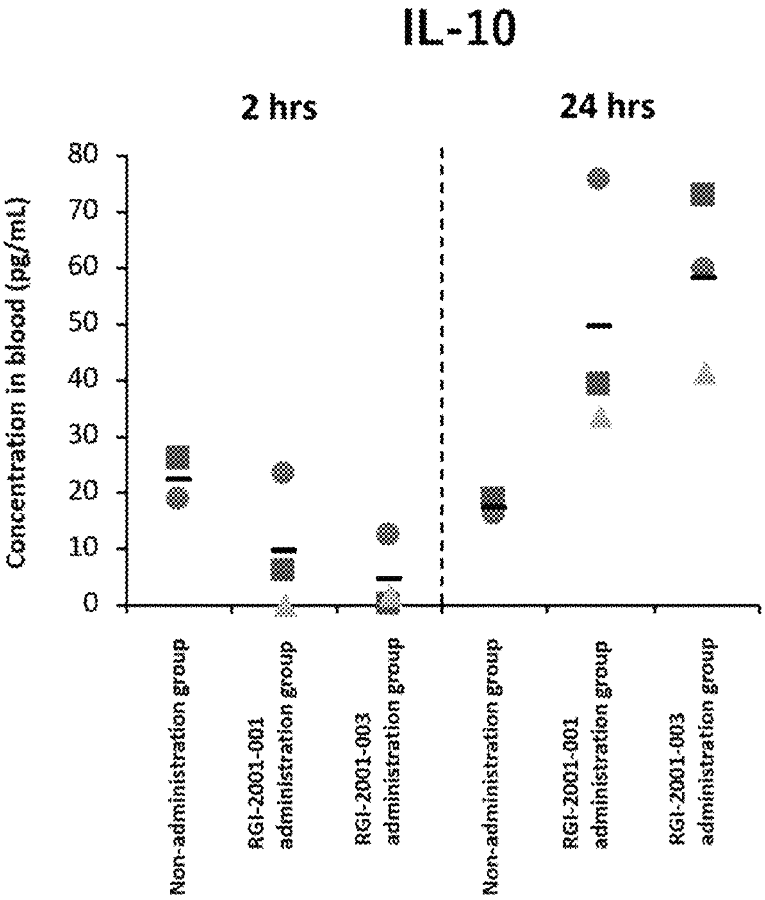
FIG. 3 shows IL-10 concentrations in the blood of mice administered with RGI-2001.

RGI-2001-001 or RGI-2001-003 was administered to the tail vein of C57BL/6 mice (♀, 8 weeks old; Clare) at a KRN7000 dose of 2 μg, and orbital blood samples were collected 2 and 24 hours later. Plasma IFN-γ, IL-4 and IL-10 concentrations were measured by the Cytometric Bead Array method (BD Biosciences). The results showed that IFN-γ was lower in the RGI-2001-003 administration group than in the RGI-2001-001 administration group, while IL-4 was higher in the RGI-200 1-003 administration group than in the RGI-2001-001 administration group (FIG. 2). On the other hand, IL-10 production was equivalent in the two groups or slightly higher in the RGI-2001-003 administration group than in the RGI-2001-001 administration group (FIG. 3). These results suggest that RGI-2001-003 is more readily taken up by marginal zone B cells than RGI-2001-001 since the average particle size of RGI-2001-003 is adjusted to around 100 nm, and as a result, RGI-2001-003 induces IL-4 production by iNKT cells more potently and induces Tregs more effectively. On the other hand, in contrast to IL-4, RGI-2001-003 was suggested to be rather less active than RGI-2001-001 in inducing IFN-γ production by iNKT cells.

[Experimental Example 5] Measurement of Particle Size

Particle size and polydispersity index of the liposome preparation produced in Experimental Example 2 were measured by a dynamic light scattering method.

<Condition 1>

The liposome preparation produced in Experimental Example 2 was diluted 1000-fold in PBS ($Ca^{2+}$ free) and analyzed for particle size and polydispersity index by DLS (dynamic light scattering, back-scattering) using Malvern's ZetaSizer Nano ZS at 25° C. The results are shown in Table 6.

TABLE 6

| | | | | Mean |
|---|---|---|---|---|
| Z average particle size(nm) | 95.74 | 96.23 | 95.79 | 95.9 |
| PdI | 0.112 | 0.102 | 0.133 | 0.116 |

<Condition 2>

The liposome preparation produced in Test Example 2 was diluted 1000-fold in PBS ($Ca^{2+}$ free) and analyzed for particle size and polydispersity index by DLS (dynamic light scattering, 90° C. scattering). The results are shown in Table 7.

TABLE 7

| | | | | Mean |
|---|---|---|---|---|
| Z average particle size(nm) | 93.05 | 92.89 | 94.55 | 93.5 |
| PdI | 0.125 | 0.127 | 0.124 | 0.125 |

From the results of these tests, the average particle size of the RGI-2001-003liposome preparation was estimated to be in the range of 92.9 to 101.0 nm when Experimental Examples 3 and 4 were performed.

Experimental Example 7

Seven patients treated with RGI-2001-003 administration in Experimental Example 3 were monitored for follow-up. As a result, one of the seven patients developed grade II acute GVHD and one developed grade I (not counted as GVHD) acute GVHD transiently, while the other five patients did not develop acute GVHD. The patient who developed grade II acute GVHD had a mild disease with lesions on the skin only, transient symptoms, and no recurrence of GVHD until one year or more after hematopoietic stem cell transplantation. These results suggest that RGI-2001-003 has an excellent suppressive effect on the development of GVHD.

TABLE 8

| # | Patient ID | Diagnosis | aGvHD*/development |
|---|---|---|---|
| 1 | 01-101/M | MDS | No |
| 2 | 02-101/M | ALL | No |
| 3 | 01-102/F | ALL | Gr 1 Day 28 |
| 4 | 02-102/F | AML | No |
| 5 | 01-103/F | CMML | No |
| 6 | 06-101/F | MDS | No |
| 7 | 01-104/M | ALL | Gr 2 Day 42 |

*Primary endpoint, Grade 2+ GvHD @100days

INDUSTRIAL APPLICABILITY

The present invention provides a liposome preparation containing a CD1d ligand that can be retained in blood for a long period and maintain a high concentration of a CD1d ligand in the blood for a long period. Since the liposome preparation of the present invention may effectively induce Tregs, excellent preventive or therapeutic effects against GVHD, organ transplant rejection, autoimmune disease or the like can be expected.

This application is based on a patent application No. 2020-201802 filed in Japan (filing date: Dec. 4, 2020), the contents of which are incorporated in full herein.

The invention claimed is:

1. A method for reducing a risk of developing graft-versus-host disease in a subject having the risk of developing graft-versus-host disease, comprising administering an effective amount of a liposome preparation containing a population of liposomes containing a CD1d ligand compound to the subject, wherein the average particle size of the population of liposomes is 90 to 110 nm, and the polydispersity index of the particle size distribution is 0.2 or less.

2. The method according to claim 1, wherein the average particle size of the population of liposomes is 92.9 to 101.0 nm.

3. The method according to claim 1, wherein the number of liposomes having a particle size of less than 50 nm in the population of liposomes is 10% or less of the total population of liposomes.

4. The method according to claim 1, wherein the number of liposomes with a particle size of more than 450 nm in the population of liposomes is 10% or less of the total population of liposomes.

5. The method according to claim 1, wherein the CD1d ligand compound is α-galactosylceramide.

6. The method according to claim 5, wherein the α-galactosylceramide is (2S,3S,4R)-1-o-(α-D-galactopyranosyl)-2-(N-hexacosanoylamino)-1,3,4-octadecanetriol.

7. The method according to claim 1, wherein the population of liposomes is contained as a liposome suspension in the liposome preparation.

8. The method according to claim 7, wherein the pH of the liposome suspension is 5.8 to 6.8.

9. The method according to claim 1, wherein the liposome preparation is administered to the subject by injection.

10. The method according to claim 1, wherein the subject having the risk of developing graft-versus-host disease is a subject who has received an allogeneic tissue or cell transplant or is scheduled to receive an allogeneic tissue or cell transplant.

11. A method for treating graft-versus-host disease in a subject who has developed graft-versus-host disease, comprising administering an effective amount of a liposome preparation containing a population of liposomes containing a CD1d ligand compound to the subject, wherein the average particle size of the population of liposomes is 90 to 110 nm, and the polydispersity index of the particle size distribution is 0.2 or less.

12. The method according to claim 11, wherein the average particle size of the population of liposomes is 92.9 to 101.0 nm.

13. The method according to claim 11, wherein the number of liposomes having a particle size of less than 50 nm in the population of liposomes is 10% or less of the total population of liposomes.

14. The method according to claim 11 wherein the number of liposomes with a particle size of more than 450 nm in the population of liposomes is 10% or less of the total population of liposomes.

15. The method according to claim 11, wherein the CD1d ligand compound is α-galactosylceramide.

16. The method according to claim 15, wherein the α-galactosylceramide is (2S,3S,4R)-1-o-(α-D-galactopyranosyl)-2-(N-hexacosanoylamino)-1,3,4-octadecanetriol.

17. The method according to claim 11, wherein the population of liposomes is contained as a liposome suspension in the liposome preparation.

18. The method according to claim 17, wherein the pH of the liposome suspension is 5.8 to 6.8.

19. The method according to claim 11, wherein the liposome preparation is administered to the subject by injection.

20. The method according to claim 11, wherein the graft-versus-host disease is caused by allogeneic hematopoietic stem cell transplantation.

* * * * *